US009725382B2

(12) United States Patent
Pretz et al.

(10) Patent No.: US 9,725,382 B2
(45) Date of Patent: Aug. 8, 2017

(54) CATALYTIC DEHYDROGENATION PROCESS

(71) Applicant: Dow Global Technologies LLC, Midland, MI (US)

(72) Inventors: Matthew T. Pretz, Lake Jackson, TX (US); Mark W. Stewart, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/034,637

(22) PCT Filed: Oct. 14, 2014

(86) PCT No.: PCT/US2014/060371
§ 371 (c)(1),
(2) Date: May 5, 2016

(87) PCT Pub. No.: WO2015/073152
PCT Pub. Date: May 21, 2015

(65) Prior Publication Data
US 2016/0272559 A1 Sep. 22, 2016

Related U.S. Application Data

(60) Provisional application No. 61/903,050, filed on Nov. 12, 2013.

(51) Int. Cl.
*C07C 5/32* (2006.01)
*C07C 5/333* (2006.01)

(52) U.S. Cl.
CPC ........ *C07C 5/3337* (2013.01); *C07C 2521/04* (2013.01); *C07C 2521/12* (2013.01);
(Continued)

(58) Field of Classification Search
CPC ... C07C 5/3337; C07C 11/06; C07C 2523/08; C07C 2523/42; C07C 2523/62;
(Continued)

(56) References Cited

U.S. PATENT DOCUMENTS 2,982,798 A * 5/1961 Hachmuth ............... B01J 23/89
585/659
4,579,716 A 4/1986 Krimbeck et al.
(Continued)

FOREIGN PATENT DOCUMENTS

WO WO 2013/009820 1/2013
WO WO 2013/126210 8/2013

OTHER PUBLICATIONS

EP Response Office Action received Dec. 21, 2016; from counterpart EP Application No. 14790934.5.
(Continued)

*Primary Examiner* — Sharon Pregler
(74) *Attorney, Agent, or Firm* — Dinsmore & Shohl LLP

(57) ABSTRACT

An improved catalytic dehydrogenation process which process comprises contacting an alkane or alkyl aromatic feedstream with a dehydrogenation catalyst under catalytic conditions in an up-flow fluidized reactor, wherein the fluidized reactor comprises one or more reactors, which catalytic conditions include a temperature within a range of from 500 to 800° C., a weight hourly space velocity within a range of from 0.1 to 1000, a gas residence time within a range of from 0.1 to 10 seconds, and, subsequent to the fluidized reactor, effecting separation of entrained catalyst from reactor effluent by use of a cyclonic separation system, wherein the improvement comprises interposing a cooling means between an up-flow fluidized reactor and the cyclonic separation system to substantially halt thermal reactions, thereby effectively increasing overall molar selectivity to alkene product is provided.

7 Claims, 1 Drawing Sheet

(52) U.S. Cl.
CPC ...... *C07C 2523/08* (2013.01); *C07C 2523/42* (2013.01); *C07C 2523/62* (2013.01); *Y02P 20/52* (2015.11)

(58) Field of Classification Search
CPC .. C07C 2521/04; C07C 2521/12; B01J 21/04; B01J 29/40
See application file for complete search history.

(56) References Cited

U.S. PATENT DOCUMENTS

| | | | |
|---|---|---|---|
| 5,190,650 A | | 3/1993 | Tammera et al. |
| 5,220,093 A | * | 6/1993 | Gartside ................ C07C 5/333 585/654 |
| 5,254,788 A | * | 10/1993 | Gartside ................ B01J 8/003 585/654 |
| 5,275,641 A | | 1/1994 | Tammera et al. |
| 2012/0123177 A1 | | 5/2012 | Pretz et al. |

OTHER PUBLICATIONS

EP Office Action dated Jun. 23, 2016; from EP counterpart Application No. 14790934.5.
PCT Search Report dated Jan. 8, 2015; from PCT counterpart Application No. PCT/US2014/60371.
PCT IPRP dated May 17, 2016; from PCT counterpart Application No. PCT/US2014/60371.
Gilbert F. Froment et al; "Thermal Cracking of Propane," Kinetics and Product Distributions, in Industrial Engineering Chemistry Process Design and Development, vol. 7, No. 3 (Jul. 1968), pp. 435-447.

\* cited by examiner

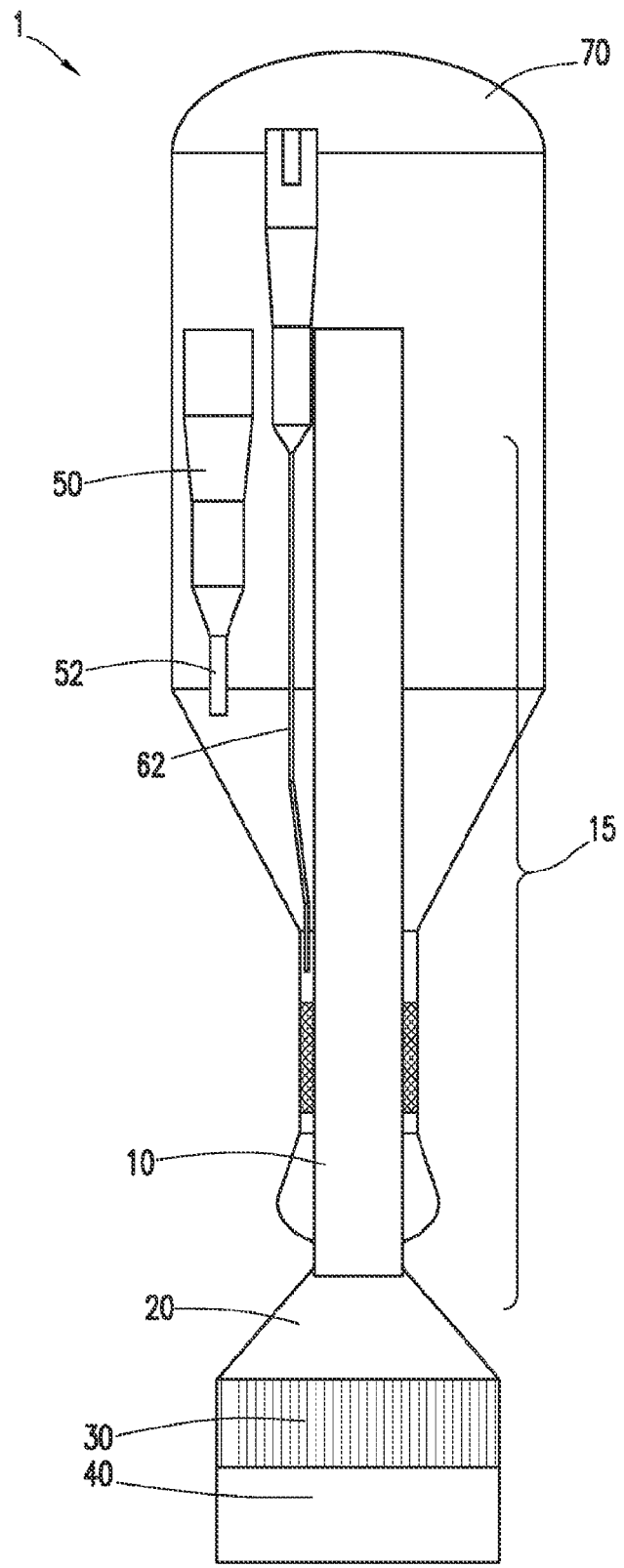

CATALYTIC DEHYDROGENATION PROCESS

FIELD OF INVENTION

The instant invention relates to an improved catalytic dehydrogenation process.

BACKGROUND OF THE INVENTION

In fluidized reaction systems for paraffin and/or alkyl aromatic dehydrogenation to the associated olefin, the thermal (gas phase) reaction of the paraffin and/or alkyl aromatic feedstock is sometimes significantly lower in selectivity than the catalytic selectivity. For example, with propane the thermal dehydrogenation to propene selectivity is about 45 to 50 mol % while the catalytic dehydrogenation to propene selectivity is about 99 mol % or greater. Likewise, ethylbenzene thermal dehydrogenation to styrene selectivity is about 67 mol % while ethylbenzene catalytic dehydrogenation selectivity is about 99 mol % or greater.

Up-flow fluidized reactors are economical means to dehydrogenate alkanes and alkyl aromatics. Specifically, risers, turbulent bed reactors, bubbling bed reactors, or fast fluidized reactors have the advantage of being able to carry out the dehydrogenation reaction at minimal residence times. However, transport of the product gas and solids to a catalyst separation system and the separation system itself increases overall gas residence time. This additional gas residence time results in less selective reaction of the feedstock resulting in a lower overall reactor selectivity to the desired product.

SUMMARY OF THE INVENTION

The instant invention is an improved catalytic dehydrogenation process. Specifically, the improved process provides an increase in the overall reactor selectivity to the associated olefin by use of quench means.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

FIG. 1 is a schematic diagram of a first embodiment of the inventive cyclonic reactor system in which the cooling means comprises a quench exchanger interposed between the fluidized reactor and a separation system riser.

DETAILED DESCRIPTION OF THE INVENTION

One embodiment of the present invention provides an improved catalytic dehydrogenation process which process comprises contacting an alkane or alkyl aromatic feed stream with a dehydrogenation catalyst which comprises gallium and platinum and carried by an alumina or alumina silica support, under catalytic conditions in an up-flow fluidized reactor system, wherein the up-flow fluidized reactor system comprises one or more reactors selected from the group consisting of bubbling bed reactors, turbulent bed reactors, fast fluidized reactors and riser reactors, which catalytic conditions include a temperature within a range of from 500 to 800° C., a weight hourly space velocity within a range of from 0.1 to 1000, a gas residence time within a range of from 0.1 to 10 seconds, and, subsequent to the fluidized reactor, effecting separation of entrained catalyst from reactor effluent by use of a cyclonic separation system, wherein the improvement comprises interposing a cooling means between the fluidized reactor and the cyclonic separation system to substantially halt thermal reactions, thereby effectively increasing overall molar selectivity to olefin product.

The improved process is useful under catalytic conditions including a temperature within a range of from 500 to 800° C. All individual values and sub-ranges from 500 to 800° C. are included herein and disclosed herein; for example, the catalytic reaction temperature can range from a lower limit of 500, 550, 600, 650, 700 or 750° C. to an upper limit of 525, 575, 625, 675, 725 or 800° C. For example, the catalytic reaction temperature may be in the range of from 500 to 800° C., or in the alternative, from 600 to 800° C., or in the alternative, from 500 to 650° C., or in the alternative, from 575 to 675° C.

The improved process is useful under catalytic conditions including a weight hourly space velocity (e.g., ratio of the mass of hydrocarbon feed rate (lb/hr) to the mass of catalyst in the catalytic reactor (lb)) within a range of from 0.1 to 1000 $hr^{-1}$. All individual values and sub-ranges from 0.1 to 1000 $hr^{-1}$ are included herein and disclosed herein; for example, the catalytic reaction weight hourly space velocity can range from a lower limit of 0.1, 1, 10, 100, or 500 $hr^{-1}$ to an upper limit of 0.5, 5, 55, 450 or 970 $hr^{-1}$. For example, the catalytic reaction weight hourly space velocity can be in the range of from 0.1 to 1000 $hr^{-1}$, or in the alternative, from 0.1 to 500 $hr^{-1}$, or in the alternative, from 400 to 990 $hr^{-1}$, or in the alternative, from 250 to 750 $hr^{-1}$.

The improved process is useful under catalytic conditions including a gas residence time within a range of from 0.1 to 10 seconds. All individual values and sub-ranges from 0.1 to 10 seconds are included herein and disclosed herein; for example, the catalytic reaction gas residence time can range from a lower limit of 0.1, 0.5, 1, 5 or 9 seconds to an upper limit of 0.4, 0.8, 3.5, 7.8 or 10 seconds. For example, the catalytic reaction gas residence time can be in the range from 0.1 to 10 seconds, or in the alternative, from 0.1 to 5 seconds, or in the alternative, from 5 to 10 seconds, or in the alternative, from 2.5 to 7.5 seconds.

In one embodiment of the invention, the improvement is applicable to catalytic paraffin dehydrogenation reactions wherein the thermal conversion is no more than 20% of the total conversion at reaction temperatures based on the calculation method described herein. All individual values and sub-ranges from no more than 20% of the total conversion are included herein and disclosed herein. For example, the thermal conversion can be 20% or less than the total conversion at reaction temperatures, or in the alternative, the thermal conversion can be 16% or less than the total conversion at reaction temperatures, or in the alternative, the thermal conversion can be 14% or less than the total conversion at reaction temperatures, or in the alternative, the thermal conversion can be 12% or less than the total conversion at reaction temperatures.

The improvement of the present invention is applicable to processes in which equal to or greater than 70 mole % of all reactions occurring are dehydrogenation.

The improved process is useful in up-flow fluidized reactor. An up-flow fluidized reactor system comprises one or more reactors selected from the group consisting of bubbling bed reactors, turbulent bed reactors, fast fluidized reactors and riser reactors. Such reactors are known in the art and any one or more or combination of such types may be used embodiments of the invention.

The up-flow fluidized reactor system further includes a cyclonic separation system. Cyclonic separation systems are known in the art and in some instances include two or more stages of cyclonic separation. Where more than one cyclonic separation device is present, the first separation device into which the fluidized stream enters is referred to a primary cyclonic separation device. The fluidized effluent from a primary cyclonic separation device may enter into a secondary cyclonic separation device. Primary cyclonic separation devices are known in the art and include, for example, primary cyclones, and systems commercially available under the names VSS, $LD^2$, and $RS^2$. Primary cyclones are described, for example, in U.S. Pat. Nos. 4,579,716; 5,190,650; and 5,275,641. In some known separation systems utilizing primary cyclones as the primary cyclonic separation device one or more set of additional cyclones, e.g. secondary cyclones and tertiary cyclones, are employed for further separation of the catalyst from the product gas. It will be understood that any primary cyclonic separation device may be used in embodiments of the invention.

The cooling means are interposed between the exit of an up-flow fluidized reactor and inlet of the cyclonic separation system. In cases where two or more up-flow reactors are used as shown in FIG. 1, the cooling means may be placed after the first up-flow reactor and, in some instances, prior to the second up-flow reactor but, in all instances, before the inlet of the cyclonic separation system. In one embodiment, a heat exchanger or quench exchanger is used. Such exchangers are well known and exemplary exchangers include shell and tube exchangers which might heat up steam, propane or product or boilers which could produce high pressure steam from liquid water and also be shell and tube or conventional catalyst coolers which use bayonet type tubes. Alternatively, coils could be used to superheat vapors or provide a heat transfer area that heats up liquid which can then be vaporized externally in a boiler vessel which holds the liquid/vapor interface. In an alternative embodiment, a cooling medium is contacted with the fluidized flow upon exiting the up-flow fluidized reactor. The cooling medium may be in any form, including liquid, solid or gas. Exemplary cooling mediums include steam, liquid water, cold catalyst, liquid hydrocarbon, cooled product gas, fuel and filler particles. The cooling medium may be a mixture of two or more cooling media. "Cold catalyst" as used as a cooling medium means dehydrogenation catalyst which is at a temperature of at least 10° C. cooler than the catalyst in the up-flow fluidized reactor. This cooler catalyst could be generated by employing a catalyst cooler on catalyst that has made a least one pass through the reactor. "Cooled product gas" as used as a cooling medium means dehydrogenated product gas which is at least 50° C. cooler than the fluidized flow exiting the up-flow fluidized reactor. "Fuel" as used as a cooling medium includes, for example, hydrogen gas, methane gas, natural gas and mixtures thereof. While the use of a cooling medium is within the scope of the invention, one advantage of using the heat exchanger is that additional gas or solids (i.e., cooling medium) that may be introduced do not have to be separated which causes larger cyclones and containment vessels for the cyclones.

The cooling means affects a decrease in the temperature of the fluidized flow. In an alternative embodiment, the instant invention provides an improved catalytic dehydrogenation process according to any of the embodiments disclosed herein, except that the cooling means decreases the temperature of the fluidized flow by at least 5° C. All individual values and sub-ranges from at least 5° C. are included herein and disclosed herein. For example, the decrease in temperature may be at least 5° C., or in the alternative, the decrease in temperature may be at least 7° C., or in the alternative, the decrease in temperature may be at least 9° C., or in the alternative, the decrease in temperature may be at least 11° C., or in the alternative, the decrease in temperature may be at least 13° C.

In an alternative embodiment, the instant invention provides an improved catalytic dehydrogenation process according to any of the embodiments disclosed herein, except that the alkane is propane and the mole ratio of thermal reaction product to catalytic reaction product that exits the reaction system where the reaction system is defined as the area of the process where the feed and products are at reaction temperature is from greater than 0:1 to less than or equal to 0.1:1. In an alternative embodiment, the instant invention provides an improved catalytic dehydrogenation process according to any of the embodiments disclosed herein, except that the alkyl aromatic is ethylbenzene and the mole ratio of thermal reaction product to catalytic reaction product is from greater than 0:1 to less than or equal to 0.1:1. In both instances of propane and ethylbenzene feedstocks, all individual values and sub-ranges from 0:1 to 0.1:1 are included herein and disclosed herein. For example, the mole ratio of thermal reaction product to catalytic reaction product can range from a lower limit of 0:1, 0.001:1, 0.005:1, 0.01:1, 0.05:1, or 0.08:1 to an upper limit of 0.003:1, 0.008:1, 0.02:1, 0.05:1, 0.08:1 or 0.1:1. The mole ratio of thermal reaction product to catalytic reaction product can range from 0 to 0.1:1, or in the alternative, from 0.05:1 to 0.1:1, or in the alternative, from 0:1 to 0.05:1, or in the alternative, from 0.01:1 to 0.08:1.

In an alternative embodiment, the instant invention provides an improved catalytic dehydrogenation process according to any of the embodiments disclosed herein, except that the overall selectivity is improved by at least 0.5 mole % in comparison to a process in which no cooling means are utilized at equivalent overall conversion. All individual values and sub-ranges from at least 0.5 mole % are included herein and disclosed herein. For example, the overall selectivity is improved by at least 0.5 mole % in comparison to a process in which no cooling means are utilized at equivalent overall conversion, or in the alternative, by at least 1 mole %, or in the alternative, by at least 1.5 mole %, or in the alternative, by at least 2 mole %.

FIG. 1 illustrates a schematic diagram of a first embodiment of the inventive cyclonic reactor system 1 in which the cooling means comprises a quench exchanger interposed between the fluidized reactor and a separation system riser. The system includes an up-flow fluidized reactor 40 in which a dehydrogenation catalyst is fluidized in a flow of an alkane or alkyl aromatic feedstock and dehydrogenated product and hydrogen. The fluidized flow passes out of the reactor 40 and through a quench exchanger 30 in which the temperature of the fluidized flow is decreased. The fluidized flow then passes upward through a frustum 20 into the transport riser 10 and then to a two stage cyclonic separation system. The cyclonic separation system further includes a primary cyclone 50 which initially separates solid catalyst from the fluidized flow with the separated catalyst exiting the primary cyclone through dipleg 52. Effluent from the primary cyclone which contains gaseous dehydrogenated product, hydrogen, unreacted feedstock and residual catalyst exits the primary cyclone 50 and enters secondary cyclone 60. Additional catalyst separation occurs in secondary cyclone 60 with the separated catalyst exiting through dipleg 62. Effluent from secondary cyclone 60 passes into separator plenum 70.

In an alternative embodiment, the fluidized flow effluent from the up-flow fluidized reactor 40 may pass into a tube, vessel or frustum 20 in which the effluent is contacted with a cooling medium. The cooling medium is injected into the bottom of the transport riser 10 or the top of the frustum 20, within the area designated by the bracket 15 shown in FIG. 1. In yet another embodiment, the fluidized flow effluent may be passed through a quench exchanger 30 and contacted with a cooling medium.

In an alternative embodiment, the improved catalytic dehydrogenation process which process comprises contacting an alkane or alkyl aromatic feedstream with a dehydrogenation catalyst which comprises gallium and platinum and carried by a alumina or alumina silica support, under catalytic conditions in an up-flow fluidized reactor, wherein the fluidized reactor comprises one or more reactors selected from the group consisting of bubbling bed reactors, turbulent bed reactors, fast fluidized reactors and riser reactors, which catalytic conditions include a temperature within a range of from 500 to 800° C., a weight hourly space velocity within a range of from 0.1 to 1000, a gas residence time within a range of from 0.1 to 10 seconds, and, subsequent to the fluidized reactor, effecting separation of entrained catalyst from reactor effluent by use of a cyclonic separation system, wherein the improvement consists essentially of interposing a cooling means between an up-flow fluidized reactor and the cyclonic separation system to substantially halt thermal reactions, thereby effectively increasing overall molar selectivity to alkene product.

EXAMPLES

The following examples illustrate the present invention but are not intended to limit the scope of the invention.

Comparative Example 1 is a model of an up-flow fluidized reactor system and cyclonic separation system as disclosed in U.S. Published Application 20120123177 which dehydrogenates propane to propylene with selectivities of from 91 to 94 mol %.

Inventive Example 1 is a model of an up-flow fluidized reactor system as in Comparative Example 1 further comprising a quench exchanger between the up-flow fluidized reactor and the cyclonic separation system.

A model is used to illustrate the potential propylene selectivity achieved with the invention.

Highly active and highly selective paraffin dehydrogenation catalysts are known. As an example, in PCT Publication No. PCT/US2012/046188, Table 1 shows propane conversions around 37.6% with catalytic selectivities of 99.3 mol %. The experiments illustrated in PCT/US2012/046188, Table 1 are conducted at 600° C. which is a temperature that exhibits very low gas phase reactions. PCT/US2012/046188, Table 6, reproduced below as Table 1, is representative of the catalytic selectivity that a very active and highly selective catalyst would be expected to produce.

TABLE 1

| Number Of Cycles | $C_3H_8$ Conversion (%) | $C_3H_6$ Selectivity (%) |
|---|---|---|
| 1 | 41.8 | 99.4 |
| 2 | 38.1 | 99.3 |
| 5 | 37.9 | 99.3 |
| 8 | 37.6 | 99.2 |
| 10 | 37.6 | 99.3 |

Alternatively, PCT/US2012/046188, Table 9, partially reproduced as Table 2 below, shows a propane conversion of 46.1% with propane to propylene selectivity of 96.4% at 625° C. with the same catalyst. At 625° C., propane shows significantly more gas phase reaction which lowers the overall measured selectivity in the experiment. In order to show this, a simple model is developed as described in Table 3.

TABLE 2

| Example | $C_3H_8$ Conversion (%) | $C_3H_6$ Selectivity (%) |
|---|---|---|
| 6 | 46.1 | 96.4 |

TABLE 3

Catalytic and Gas Phase Propane → Propylene Selectivity Model

| Thermal Kinetics | | Units | Catalytic Reactor Lab |
|---|---|---|---|
| ln(a) | 33.18 | | |
| Ea/R | −33769.5 | | |
| | Propane Remaining | mol % | 100 |
| | Average Reaction Temperature | ° C. | 625 |
| | Residence Time | Seconds | 2 |
| | Catalytic Conversion | % | 44 |
| | Catalytic Selectivity | mol % | 99.3 |
| | Thermal Rate, k | mol/sec | 0.01197 |
| | Thermal Conversion | % | 2.4 |
| | Thermal Converted | % | 2.4 |
| | Thermal Selectivity | mol % | 45 |
| | Total Conversion | % | 46.4 |
| | Total Selectivity | mol % | 96.5 |

The catalytic selectivity was taken from Table 1 which shows a selectivity of 99.3 mol %. The thermal selectivity of propane is taken from "Thermal Cracking of Propane.Kinetics and Product Distributions" in Industrial Engineering Chemistry Process Design and Development by Froment (1968), Page 440. The thermal reaction rate is calculated using the Arrenhius equation as shown below in Eqn. (1) using the Laider coefficients described by Froment in "Thermal Cracking of Propane. Kinetics and Product Distributions"

$$k = Ae^{-E_a/(RT)} \quad (1)$$

The application of the Arrenhius equation is taken from the re-arrangement of Eqn. (1) as shown in Eqn (2) below. This allows the molar rate of reaction per second to be calculated, k.

$$\ln(k) = \frac{-E_a}{R}\frac{1}{T} + \ln(A) \quad (2)$$

The thermal reaction rate is then taken on the propane that is available at 45 mol % selectivity. The catalytic performance is solved for to achieve the measured total conversion. The resulting overall selectivity then should be close the measured value in the experiment. In this case, the model shows 96.5 mol % selectivity versus a measured 96.4 mol %.

The current invention is modeled with the methodology described above by combining the predicted catalytic performance in a catalytic reactor with the associated gas phase reaction kinetics.

Reactor Sizing Criteria

Upper Transport Riser

The height of the transport section is based on the physical layout of the unit. Because the unit physically consists of a hydrocarbon stripper and a two stage cyclone separation system, a minimum distance from the fast fluidized/turbulent bed reactor to the cyclone exists. This increases gas residence times resulting in thermal cracking of propane and degradation of products.

The diameter of this upper section is set based on a maximum value of ~35-80 ft/s to quickly transport the catalyst and gas to the cyclones without causing un-necessary erosion of the equipment or attrition of the catalyst.

Fast Fluidized/Turbulent Bed Reactor

The lower reactor diameter and height is set based on a desired catalyst loading to achieve the desired catalytic conversion in the minimum gas residence time possible. The model described above is applied to Comparative Example 1. In Comparative Example 1, a catalytic conversion of 37.58% is considered at the expected catalytic selectivity in the lower reactor and 3.31% in the transport riser. The thermal reaction is then taken on the remaining propane in the reactor, transport riser, and cyclones after the catalytic reaction in each zone. This is an approximation of the selectivity as the thermal reaction and catalytic reaction will occur simultaneously. The result is that the reaction system can achieve 45.5% conversion with an overall selectivity of 93.8 mol %, as shown in Table 4.

Alternatively, the model can be applied to Reactor Type B. The model is applied to Inventive Example 1, which is shown in Table 5. In Inventive Example 1, a quench exchanger or direct quench introduction can be applied directly following the fast fluidized/turbulent bed reactor. By immediately quenching the catalyst and gas, the overall conversion drops from 45.5% to 43.3% but the selectivity increases from 93.8% to 96.2%. This is almost a 2.5 mol % improvement over reactor type A. In fact, the incremental selectivity of the additional 2.2% conversion was only 45 mol % which is very poor and not desirable.

In addition to solely improving the overall selectivity of the process, the gas residence time in the catalytic reactor can be increased to bring the overall conversion level up to the same levels as shown with reactor type A. If the conversion is increased, the result can be found in Table 6. In this example, 45.5% propane conversion is achieved with an overall selectivity of 96.1 mol %.

The use of a quench exchanger or direct quench into the riser enables selectivities to the desired olefin product to be increased. Alternatively, the reaction temperature could be raised to achieve higher conversions at similar selectivities to cases in which a quench exchanger is not used.

TABLE 4

| Thermal Kinetics | Units | Catalytic Reactor, Fast Fluidized/Turbulent | Transport Riser to Cyclones | Cyclones, 2 Stage Close-Coupled System |
|---|---|---|---|---|
| Propane Remaining | mol % | 100 | 60.6 | 56.1 |
| Avg Reaction Temperature | C. | 625 | 620 | 620 |
| Residence Time | Sec | 1.5 | 2.2 | 3.1 |
| Catalytic Conversion | % | 37.58 | 3.31 | 0 |
| Catalytic Selectivity | mol % | 99.3 | 99.3 | 99.3 |
| Thermal Rate | mol/sec | 0.01197 | 0.00970 | 0.00970 |
| Thermal Conversion | % | 1.8 | 2.1 | 3.0 |
| Thermal Converted | % | 1.8 | 1.2 | 1.7 |
| Thermal Selectivity | mol % | 45 | 45 | 45 |
| Total Conversion | % | 39.4 | 43.9 | 45.5 |
| Total Selectivity | mol % | 96.8 | 95.6 | 93.8 |
| Total Yield | mol % | | | 42.7 |
| Incremental Selectivity vs Ex B | mol % | | | 77.9 |

TABLE 5

| | | Catalytic Reactor, Fast Fluidized/Turbulent | Quench Exchanger | Transport Riser to Cyclones | Cyclones, 2 Stage Close-Coupled System |
|---|---|---|---|---|---|
| Propane Remaining | mol % | 100 | 60.6 | 57.1 | 56.9 |
| Avg Reaction Temperature | C. | 625 | 610 | 580 | 580 |
| Residence Time | sec | 1.5 | 0.5 | 2.2 | 3.1 |
| Catalytic Conversion | % | 37.58 | 3.31 | 0 | 0 |
| Catalytic Selectivity | mol % | 99.3 | 99.3 | 99.3 | 99.3 |
| Thermal Rate | mol/sec | 0.01197 | 0.00632 | 0.00165 | 0.00165 |
| Thermal Conversion | % | 1.8 | 0.3 | 0.4 | 0.5 |
| Thermal Converted | % | 1.8 | 0.2 | 0.2 | 0.3 |
| Thermal Selectivity | mol % | 45 | 45 | 45 | 45 |
| Total Conversion | % | 39.4 | 42.9 | 43.1 | 43.3 |
| Total Selectivity | mol % | 96.8 | 96.8 | 96.6 | 96.2 |
| Total Yield | mol % | | | | 41.7 |

TABLE 6

| | | Catalytic Reactor, Fast Fluidized/Turbulent | Quench Exchanger | Transport Riser to Cyclones | Cyclones, 2 Stage Close-Coupled System |
|---|---|---|---|---|---|
| Propane Remaining | mol % | 100 | 55.1 | 55.0 | 54.8 |
| Avg Reaction Temperature | C. | 625 | 610 | 580 | 580 |
| Residence Time | sec | 1.7 | 0.5 | 2.2 | 3.1 |
| Catalytic Conversion | % | 42.8 | 0 | 0 | 0 |
| Catalytic Selectivity | mol % | 99.26 | 99.26 | 99.26 | 99.26 |
| Thermal Rate | mol/sec | 0.01197 | 0.00632 | 0.00165 | 0.00165 |
| Thermal Conversion | % | 2.0 | 0.3 | 0.4 | 0.5 |

TABLE 6-continued

|  |  | Catalytic Reactor, Fast Fluidized/ Turbulent | Quench Exchanger | Transport Riser to Cyclones | Cyclones, 2 Stage Close-Coupled System |
|---|---|---|---|---|---|
| Thermal Converted | % | 2.0 | 0.2 | 0.2 | 0.3 |
| Thermal Selectivity | mol % | 45 | 45 | 45 | 45 |
| Total Conversion | % | 44.9 | 45.0 | 45.2 | 45.5 |
| Total Selectivity | mol % | 96.8 | 96.6 | 96.4 | 96.1 |
| Total Yield | mol % |  |  |  | 43.7 |

The present invention may be embodied in other forms without departing from the spirit and the essential attributes thereof, and, accordingly, reference should be made to the appended claims, rather than to the foregoing specification, as indicating the scope of the invention.

We claim:

1. An improved catalytic dehydrogenation process which process comprises contacting an alkane or alkyl aromatic feedstream with a dehydrogenation catalyst which comprises gallium and platinum and carried by a alumina or alumina silica support, under catalytic conditions in an up-flow fluidized reactor, wherein the fluidized reactor comprises one or more reactors selected from the group consisting of bubbling bed reactors, turbulent bed reactors, fast fluidized reactors, and riser reactors, which catalytic conditions include a temperature within a range of from 500 to 800° C., a weight hourly space velocity within a range of from 0.1 to 1000, a gas residence time within a range of from 0.1 to 10 seconds, and, subsequent to the fluidized reactor, effecting separation of entrained catalyst from reactor effluent by use of a cyclonic separation system, wherein the improvement comprises cooling the entrained catalyst and the reactor effluent before effecting separation of the entrained catalyst from the reactor effluent, wherein cooling the entrained catalyst and the reactor effluent substantially halts thermal reactions, thereby effectively increasing overall molar selectivity to alkene product.

2. The catalytic dehydrogenation process of claim 1, wherein the thermal conversion is no more than 20% of the total conversion at reaction temperatures.

3. The catalytic dehydrogenation process of claim 1, wherein cooling the entrained catalyst and the reactor effluent comprises at least one of (i) passing the entrained catalyst and the reactor effluent through a quench exchanger situated between the fluidized reactor and the cyclonic separation system; and (ii) injecting a cooling medium into a zone between the fluidized reactor and the cyclonic separation system.

4. The catalytic dehydrogenation process of claim 3, wherein the alkane and/or alkyl aromatic is selected from propane and/or ethylbenzene and the mole ratio of thermal reaction product to catalytic reaction product is greater than 0:1 and less than or equal to 0.1:1.

5. The catalytic dehydrogenation process of claim 1, wherein cooling the entrained catalyst and the reactor effluent comprises injecting a cooling medium into a zone between a reaction zone of the fluidized reactor and a riser, wherein the cooling medium comprises at least one of steam, liquid water, cold catalyst, liquid hydrocarbon, cooled product gas, fuel, and filler particles.

6. The catalytic dehydrogenation process of claim 1, wherein the overall selectivity is improved by at least 0.5 mole % compared to a process having equivalent overall conversion but not including cooling the entrained catalyst and the reactor effluent.

7. The catalytic dehydrogenation process of claim 5, wherein the cooling medium comprises at least one of steam and liquid water.

* * * * *